(12) United States Patent
Gao et al.

(10) Patent No.: US 12,071,615 B2
(45) Date of Patent: *Aug. 27, 2024

(54) BLOOD CELL LYSIS REAGENT

(71) Applicant: Gen-Probe Incorporated, San Diego, CA (US)

(72) Inventors: Kui Gao, San Diego, CA (US); Jijumon Chelliserry, San Diego, CA (US); Jeffrey Linnen, Poway, CA (US)

(73) Assignee: Gen-Probe Incorporated, San Diego, CA (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/485,599

(22) Filed: Sep. 27, 2021

(65) Prior Publication Data

US 2022/0002707 A1    Jan. 6, 2022

Related U.S. Application Data

(63) Continuation of application No. 16/094,070, filed as application No. PCT/US2017/029671 on Apr. 26, 2017, now Pat. No. 11,162,091.

(60) Provisional application No. 62/328,358, filed on Apr. 27, 2016.

(51) Int. Cl.
| | | |
|---|---|---|
| C12N 15/10 | (2006.01) | |
| C12Q 1/6806 | (2018.01) | |
| C12Q 1/70 | (2006.01) | |

(52) U.S. Cl.
CPC ....... C12N 15/1003 (2013.01); C12Q 1/6806 (2013.01); C12Q 1/70 (2013.01); *Y02A 50/30* (2018.01)

(58) Field of Classification Search
CPC .... C12N 15/1003; C12Q 1/6806; C12Q 1/70; C12Q 2525/161; C12Q 2527/125; C12Q 2531/143; C12Q 2565/501; Y02A 50/30
See application file for complete search history.

(56) References Cited

U.S. PATENT DOCUMENTS

| | | |
|---|---|---|
| 4,843,155 A | 6/1989 | Chomczynski |
| 5,346,994 A | 9/1994 | Chomczynski |
| 5,595,876 A | 1/1997 | Rakestraw |
| 5,786,208 A | 7/1998 | Clark |
| 5,945,515 A | 8/1999 | Chomczynski |
| 5,973,137 A | 10/1999 | Heath |
| 6,111,096 A | 8/2000 | Laugharn, Jr. |
| 7,601,491 B2 | 10/2009 | Collis |
| 7,670,768 B1 | 3/2010 | Heath |
| 10,093,989 B2 | 10/2018 | Chelliserry |
| 10,689,713 B2 | 6/2020 | Chelliserry |
| 11,162,091 B2* | 11/2021 | Gao .................... C12Q 1/6806 |
| 2001/0041332 A1 | 11/2001 | Hillebrand |
| 2002/0068280 A1 | 6/2002 | Fairman |
| 2003/0157492 A1 | 8/2003 | Heath |
| 2004/0142318 A1 | 7/2004 | Wu |
| 2005/0208501 A1 | 9/2005 | Goldrick |
| 2006/0063185 A1 | 3/2006 | Vannier |
| 2006/0105372 A1 | 5/2006 | Bair |
| 2007/0161015 A1 | 7/2007 | Zheng |
| 2007/0281317 A1 | 12/2007 | Becker |
| 2009/0081678 A1 | 3/2009 | Ryan |
| 2009/0143572 A1 | 6/2009 | Inomata |
| 2009/0233285 A1 | 9/2009 | Schalken |
| 2010/0129878 A1 | 5/2010 | Parthasarathy |
| 2010/0196903 A1 | 8/2010 | Darby |
| 2011/0081645 A1 | 4/2011 | Linnen |
| 2011/0092687 A1 | 4/2011 | Bendzko |
| 2011/0183398 A1 | 7/2011 | Dasaratha |
| 2012/0164644 A1 | 6/2012 | Neely |
| 2014/0057247 A1 | 2/2014 | Rogacs |
| 2014/0087359 A1 | 3/2014 | Njoroge |
| 2018/0143115 A1 | 5/2018 | Linnen |

FOREIGN PATENT DOCUMENTS

| | | |
|---|---|---|
| DE | 10219117 | 10/2003 |
| DE | 10219119 | 11/2003 |
| EP | 0270017 | 6/1988 |
| JP | 2002535014 | 10/2002 |
| JP | 2007132776 | 5/2007 |
| JP | 2009538148 | 11/2009 |
| WO | 0034463 | 6/2000 |
| WO | 0044940 | 8/2000 |
| WO | 02055737 | 7/2002 |
| WO | 2009042457 | 4/2009 |
| WO | 2009042547 | 4/2009 |
| WO | 2010039987 | 4/2010 |
| WO | 2012054588 | 4/2012 |
| WO | 2016038526 | 3/2016 |
| WO | 2016064887 | 4/2016 |
| WO | 2016183282 | 11/2016 |

OTHER PUBLICATIONS

Kerr, R.J.S., et al., Qualitative Human Immunodeficiency Virus RNA Analysis of Dried Blood Spots for Diagnosis of Infections in Infants, Journal of Clinical Microbiology 47(1):220-222, Jan. 2009.
EPO Extended European Search Report dated Sep. 24, 2020, issued in European Application No. 20176793.6.
PCT International Preliminary Report on Patentability dated Mar. 28, 2018, issued in International Application No. PCT/US2017/029671, filed Apr. 26, 2017.
PCT Written Opinion dated Sep. 15, 2017, issued in International Application No. PCT/US2017/029671, filed Apr. 26, 2017.

(Continued)

*Primary Examiner* — Narayan K Bhat
(74) *Attorney, Agent, or Firm* — Christensen O'Connor Johnson Kindness PLLC; Jeffrey E. Landes

(57) ABSTRACT

Disclosed herein are lysis reagents for lysing red blood cells, thereby releasing an analyte, such as RNA from a host or pathogen, in a form suitable for analysis. The reagent includes at least a buffer, a detergent and one or both of a chloride containing salt and an anti-coagulant. The reagent serves to lyse blood cells, protect the released analyte from degradation in the lysate, and is compatible with subsequent steps for analysis of the analyte such as target capture, amplification, detection, or sequencing.

20 Claims, No Drawings

Specification includes a Sequence Listing.

(56) References Cited

OTHER PUBLICATIONS

PCT International Search Report dated Sep. 15, 2017, in International Application No. PCT/US2017/029671, filed Apr. 26, 2017.
USPTO Non-Final Rejection issued Jan. 19, 2018, in U.S. Appl. No. 14/918,131, filed Oct. 20, 2015.
USPTO Final Rejection issued May 16, 2018, in U.S. Appl. No. 14/918,131, filed Oct. 20, 2015.
USPTO Notice of Allowance issued Jun. 4, 2018, in U.S. Appl. No. 14/918,131, filed Oct. 20, 2015.
EPO Extended European Search report dated Apr. 23, 2018, issued in European Application No. 15851970.2.
PCT International Preliminary Report on Patentability dated Apr. 25, 2017, issued in International Application No. PCT/US2015/056480, filed Oct. 20, 2015.
PCT Written Opinion dated Dec. 29, 2015, issued in International Application No. PCT/US2015/056480, filed Oct. 20, 2015.
PCT International Search Report dated Jan. 4, 2016, issued in International Application No. PCT/US2015/056480, filed Oct. 20, 2015.
UKIPO Combined Search and Examination Report dated Jul. 22, 2016, issued in United Kingdom Application No. GB1518583.8.
UKIPO Examination Report dated Mar. 22, 2018, issued in United Kingdom Application No. GB1518583.8.
Bossuyt, et al., "Comparative Analysis of Whole Blood Lysis Methods for Flow Cytometry," Communications in Clinical Cytometery, 1997, 30:124-133, National Institute of Health, USA.
Chomczynski, et al., "Single-Step Method of RNA Isolation by Acid Guanidinium Thiocyanate-Phenol-Choroform Extraction," Analytical Biochemistry, 1987, 162:156-159, Academic Press, Inc., USA.
Ghatak, et al., "A Simple Method of Genomic DNA Extraction from Human Samples for PCR-RFLP Analysis," Journal of Biomolecular Techniques, 2013, 24:224-231.
Gunther, et al., "Implementation of a proficiency testing for the assessment of the preanalytical phase of blood samples used for RNA based analysis," Clinica Chimica Acta, 2012, pp. 779-786.
Mahalanabis et al., "Cell lysis and DNA extraction of gram-positive and gram-negative bacteria from whole blood in a disposable microfluidic chip," Royal Society of Chemistry, 2009, 9:2811-2817, Department of Biomedical Engineering, USA.
McCoy, et al., "Human Erythrocate Lysing Solution (Ammonium Chloride Lysing Solution, 10x)," 1998, Handling storage and presentation of hman cells, Curr. Protocol. Cytom., XP055402846.1.
Ovstebo et al., "Quantification of relative changes in specific mRNAs from frozen whole blood—methodological considerations and clinical implications," Clin Chem Lab Med, 2007, 45(2):171-176.
Pazzagli, et al., "SPIDIA-RNA: First external quality assessment for the pre-analytical phase of blood samples used for RNA based analyses," Methods, 2013, pp. 20-31.
Roche, "Red Blood Cell Lysis Buffer," Cat. No. 11 814 389 001, 2011.
Teal, et al., "A New Real-Time PCR Assay for Improved Detection of the Parasite Babesia microti," Journal of Clinical Microbiology, 2011, 50(3).
Wang, et al., "Purification of genomic DNA from human whole blood by isopropanol-fractionation with concentrated NaI and SDS," Oxford University Press, 1994, 22(9):1774-1775, Nucleic Acid Research.
Zheng, et al., "Sensitive and Quantitative Measurement of Gene Expression Directly from a Small Amount of Whole Blood," Clinical Chemistry, 2006, 52:7.
UKIPO Combined Search and Examination Report dated Feb. 5, 2018, issued in United Kingdom Application No. GB1800795.5.
Japanese Notice of Reasons for Rejection mailed Jan. 19, 2023, in Japanese Patent Application No. 2021-084650, filed Apr. 26, 2017, 11 pages.

* cited by examiner

BLOOD CELL LYSIS REAGENT

CROSS REFERENCE TO RELATED APPLICATIONS

The present application is a continuation of U.S. patent application Ser. No. 16/094,070, filed on Oct. 16, 2018, now issued as U.S. Pat. No. 11,162,091, which is a national stage entry of International Application No. PCT/US2017/029671, filed on Apr. 26, 2017, which claims the benefit, under 35 U.S.C. § 119(e), of U.S. Provisional Application No. 62/328,358, filed on Apr. 27, 2016. The entire contents of each of the foregoing applications are hereby incorporated by reference.

REFERENCE TO SEQUENCE LISTING

The instant application contains a Sequence Listing which has been submitted in ASCII format via EFS-Web and is hereby incorporated by reference in its entirety. Said ASCII Copy, created on Sep. 23, 2021, is named "Dia-0023-02-Seq-Listing_ST25" and is 2,978 bytes in size.

BACKGROUND

Although there are commercial assays for detecting RNA in blood, the RNA detected in such assays is usually present in extracellular forms, such as HIV or HCV particles in the blood. Detection of RNA or other target molecules from within blood cells, and particularly from within red blood cells is more challenging. Reagents used in lysis may interfere with subsequent processing as many non-target molecules released by lysis, particularly nucleases or proteases, may degrade target molecules.

The intrinsic instability of RNA and presence of RNAses in whole blood makes isolation of RNA a difficult task. The use of high purity, intact RNA facilitates sensitive clinical diagnostic assays. Existing approaches typically involve several sequential steps: a step to disrupt the cells, a step to denature the proteins, another step for the stabilization and protection of RNA from RNAses, and then a step for isolation of the RNA Tetradecyltrimethylammonium oxalate (TDTMAO) is commonly used for transport, storage and processing of blood (U.S. Pat. Nos. 6,602,718 and 6,617,170). This quaternary amine is contained, for example, in the PAXgene™ Blood RNA System (BD Biosciences) and works by penetrating the cell and stabilizing intracellular target RNA. The RNA can then be later purified and analyzed from the components of whole blood using standard techniques. Methods for lysing cells and inhibiting RNases using guanidinium salts are also known (Chomczynski et al. (1987) Anal. Biochem. 162, 156-159).

SUMMARY

Provided herein is a reagent comprising a buffer and a detergent, and further comprising a salt, an anti-coagulant, or both. In some embodiments, the reagent comprises a buffer, a salt and a detergent. In some embodiments, the reagent comprises a buffer, a salt and an anti-coagulant. In some embodiments, a reagent is provided comprising one or more of a salt, a buffer, a detergent, and an anti-coagulant. In some embodiments, a reagent is provided comprising a salt, a detergent and an anti-coagulant. In some embodiments, a reagent is provided comprising a buffer, a salt and a detergent. In some embodiments, a reagent is provided comprising a buffer, a salt, a detergent, and an anti-coagulant.

In some embodiments, the buffer is a sodium bicarbonate buffer. In some embodiments, the buffer is a TRIS (2-Amino-2-(hydroxymethyl)-1,3-propanediol) buffer. In some embodiments, the buffer is a sodium bicarbonate buffer. In some embodiments, the buffer is a sodium phosphate buffer. In some embodiments, the buffer is a sodium bicarbonate buffer in the reagent in a concentration from about 5 mM to about 30 mM, from about 10 mM to about 20 mM, about 10 mM to about 15 mM, or from about 15 mM to about 20 mM. In some embodiments, the buffer is a TRIS buffer in the reagent at a concentration from about 75 mM to about 150 mM, from about 75 mM to about 125 mM, from about 100 mM to about 125 mM, or from about 90 mM to about 110 mM. In some embodiments, the buffer is a sodium phosphate ($Na_3PO4$) buffer in the reagent at a concentration from about 5 mM to about 30 mM, from about 10 mM to about 20 mM, about 10 mM to about 15 mM, or from about 15 mM to about 20 mM. In some embodiments, the concentration of sodium phosphate in the reagent is from about 8 mM to about 40 mM, from about 10 mM to about 33 mM, from about 15 mM to about 30 mM, about 30 mM, or about 15 mM. In some embodiments, the concentration of sodium phosphate monobasic in the reagent is from about 8 mM to about 40 mM, from about 10 mM to about 33 mM, from about 15 mM to about 30 mM, about 30 mM, or about 15 mM. In some embodiments, the concentration of sodium phosphate dibasic in the reagent is from about 8 mM to about 40 mM, from about 10 mM to about 33 mM, from about 15 mM to about 30 mM, about 30 mM, or about 15 mM. Ranges include all whole and partial numbers therein.

In some embodiments, the anti-coagulant is one or more of EDTA ((Ethylenedinitrilo)tetraacetic acid), EDTA-$Na_2$ (Disodium ethylenediaminetetraacetate dihydrate), EGTA (Ethylene-bis(oxyethylenenitrilo)tetraacetic acid), heparin, or citrate. In some embodiments, the anti-coagulant comprises an EDTA in the reagent at a concentration from about 0.05 mM to about 15 mM, from about 0.1 mM to about 10 mM, or from about 0.5 mM to about 5 mM. In some embodiments, the anti-coagulant is EDTA in the reagent at a concentration from about 0.05 mM to about 15 mM, from about 0.1 mM to about 10 mM, or from about 0.5 mM to about 5 mM. In some embodiments, the anti-coagulant is EDTA-$Na_2$ in the reagent at a concentration from about 0.05 mM to about 15 mM, from about 0.1 mM to about 10 mM, or from about 0.5 mM to about 5 mM. In some embodiments, the anti-coagulant is EGTA in the reagent at a concentration from about 0.05 mM to about 15 mM, from about 0.1 mM to about 10 mM, or from about 0.5 mM to about 5 mM. Ranges include all whole and partial numbers therein.

In some embodiments, the salt comprises one or more of the following ions: a sodium ion, a potassium ion, an ammonium ion, a magnesium ion, a lithium ion, and a chloride ion. In some embodiments, the salt is magnesium chloride, ammonium chloride, potassium chloride, or sodium chloride. In some embodiments, the salt comprises a chloride ion and one of a magnesium ion, sodium ion or potassium ion, and the concentration of the salt in the reagent is from about 10 mM to about 50 mM, from about 15 mM to about 40 mM, or from about 20 mM to about 35 mM. In some embodiments, the salt is ammonium chloride in the reagent at a concentration from about 100 mM to about 500 mM, from about 200 mM to about 350 mM, or from about 250 mM to about 300 mM. Ranges include all whole and partial numbers therein.

In some embodiments, the detergent is one of lithium lauryl sulfate (LLS), nonyl phenoxypolyethoxylethanol (NP 40), sodium dodecyl sulfate (SDS), and Triton-X 100. In some embodiments, the detergent is an anionic detergent. In some embodiments, the detergent is LLS or SDS. In some embodiments, the detergent is present in the reagent at a concentration that is greater than about 1.5% (v/v or w/v). In some embodiments, the detergent is present in the reagent at a concentration that is less than about 15.5% (v/v or w/v). In some embodiments, the detergent is present in the reagent at a concentration of from about 2% to about 15% (v/v or w/v). In some embodiments, the detergent is present in the reagent at a concentration from about 2% to about 15% (v/v or w/v). In some embodiments, the detergent is LLS and the concentration of LLS in the reagent is from about 2% to about 15% (w/v), from about 4% to about 10% (w/v), or from about 5% to about 8% (w/v). In some embodiments, the detergent is LLS and is present in the reagent at about 14 mM to about 50 mM. Ranges include all whole and partial numbers therein.

In some embodiments, the pH of the reagent is greater than a pH of 5.5. In some embodiments, the pH of the reagent is less than a pH of 10.5. In some embodiments, the pH of the reagent is from about 6.0 to about 10.0. In some embodiments, the pH of the reagent is from about 6.5 to about 8.0, or from about 7.0 to about 8.0, or from about 7.2 to about 7.6, or from about 6.7 to about 7.5, or about 6.7, or about 7.3 or about 7.5. Ranges include all whole and partial numbers therein.

In some embodiments of the reagent, the concentration of sodium bicarbonate is 14 mM, the concentration of ammonium chloride is 250 mM, the concentration of LLS is 8% (w/v), the concentration of EDTA is from about 0.1 mM to about 10 mM, and the pH is 7.2-7.6. In some embodiments of the reagent, the buffer is selected from the group consisting of sodium bicarbonate, sodium phosphate and TRIS, the detergent is from about 5% to about 10% (v/v or w/v), the pH is from about 6.5 to about 8.0, and the salt is selected from the group consisting of magnesium chloride, ammonium chloride, and potassium chloride. In some embodiments of the reagent, the buffer is selected from the group consisting of sodium phosphate and TRIS and the salt is selected from the group consisting of magnesium chloride and ammonium chloride. In some aspects of this embodiment, the concentration of anti-coagulant is about 0 mM to about 1 mM. In some further aspects of this embodiment, the detergent is LLS at a concentration from about 6% to about 10% (w/v). In some further aspects of this embodiment, the buffer is TRIS at a concentration from about 90 mM to about 110 mM and the pH of the reagent is from about 7.2 to about 7.5. In some further aspects of this embodiment, the anti-coagulant is at a concentration of about 0.1 mM to about 5 mM and is EGTA, EDTA, EDTA-Na$_2$ or a combination thereof.

In some embodiments, the reagent is admixed with blood cells, with red blood cells or with products derived from red blood cells. In certain embodiments, the reagent is admixed with whole blood. In some embodiments, the reagent is admixed with whole blood in a ratio of about 1:1 (v/v) to about 4:1 (v/v), including all whole numbered and partial numbered ratios there between. In some embodiments, the reagent is admixed with whole blood in a ratio of 3:1 (v/v). In some embodiments, the whole blood is human whole blood, non-human whole blood, or a mixture thereof.

Further provided herein is a method of analyzing an analyte from blood cells comprising: (a) contacting blood cells with a reagent comprising a buffer, a salt and a detergent, the reagent being effective to lyse the blood cells and inhibit degradation of analyte released from the blood cells; and (b) analyzing the analyte released from the blood cells.

In some methods, the target is a pathogen-derived target. In some methods, the target is RNA.

In some methods, analyzing the target comprises a nucleic acid assay. In some methods, analyzing the target comprises contacting the released target with a capture probe and an immobilized probe, the capture probe having a first segment complementary to the target, and a second segment complementary to the immobilized probe, wherein the target binds to the capture probe, and wherein the bound capture probe binds to the immobilized probe. Some methods further comprise performing a transcription mediated amplification of the target and detecting the resulting amplification product with a detection probe.

Some methods are performed without a centrifugation step to separate the reagent from the target released from the blood cells.

BRIEF DESCRIPTION OF THE SEQUENCES

SEQ ID NO:1 sets forth the nucleic acid sequence of a non T7 primer.

SEQ ID NO:2 sets forth the nucleic acid sequence of a T7 primer.

SEQ ID NO:3 sets forth the nucleic acid sequence of an acridinium ester (AE) probe.

SEQ ID NO:4 sets forth the nucleic acid sequence of a target capture oligonucleotide (TCO) probe.

DEFINITIONS

Pathogens include viruses, bacteria, protozoa, fungi, and other microorganisms responsible for disease in humans and other animals.

An analyte (sometimes referred to herein as a target) can be a single type of molecule, such as a protein or a nucleic acid, or a class of molecules, such as any protein or RNA from a parasite or any protein or RNA from blood cells. Multiple distinct analytes can also be analyzed, such as an RNA analyte and a protein analyte, or two distinct RNA analytes, such as two different mRNA analytes, or an mRNA analyte and an rRNA analyte. Analytes include endogenous components of blood cells and components arising as a result of pathogenic infection of infected blood cells and are typically encoded by the infecting pathogen (i.e., "pathogenic" or "pathogen-derived" analytes).

A lysis reagent is reagent, often provided in the form of a solution, effective for inducing lysis of blood cells in whole blood, including lysis of red blood cells or red blood cell products such as pelleted red blood cells.

Detergents, are surface acting agents effective in solubilizing hydrophobic molecules. Generally, these are water-soluble surface-active agents comprised of a hydrophobic portion, usually a long alkyl chain, attached to hydrophilic or water solubility enhancing functional groups. Detergents include anionic detergents, cationic detergents, zwitterionic detergents, non-ionic detergents, and anti-foaming agents.

Anti-coagulants inhibit clotting of whole blood. Anti-coagulants include heparins and calcium chelating agents. Heparins activate antithrombin III, which inhibits the activity of thrombin and other proteases involved in blood clotting. Calcium chelating agents, such as the EDTAs, the EGTAs and citrates, bind calcium ions required for blood clotting.

A buffer refers to a weak acid or weak base used to maintain the pH of a solution.

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, (The Biochemistry of the Nucleic Acids 5-36, Adams et al., ed., 11.sup.th ed., 1992; van Aerschott et al., 1995, Nucl. Acids Res. 23(21): 4363-70), pyrimidine or purine derivatives, (Hill et al., 1998, Proc. Natl. Acad. Sci. USA 95(8):4258-63, Lin and Brown, 1992, Nucl. Acids Res. 20(19):5149-52), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U or T and G) in a defined portion of a larger oligomer. The resulting oligomer is actually a population of oligomers whose finite number of members is determined by the length and number of bases making up the random portion (e.g., $2^6$ oligomers in a population of oligomers that contains a 6-nt random sequence synthesized by using 2 different bases).

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect (i.e., exact) or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Separating" or "isolating" or "purifying" refers to removing one or more components from a complex mixture, such as a sample. Preferably, a separating, isolating or purifying step removes at least 70%, preferably at least 90%, and more preferably at least 95% w/w of the nucleic acid analytes from other sample components. A separating, isolating or purifying step may optionally include additional washing steps to remove non-analyte sample components.

"Release" of a capture hybrid refers to separating one or more components of a capture hybrid from each other, such as separating a nucleic acid analyte from a capture probe, and/or a capture probe from an immobilized probe. Release of the nucleic acid strand separates the analyte from other components of a capture hybrid and makes the analyte available for binding to a detection probe. Other components of the capture hybrid may remain bound, e.g., the capture probe strand to the immobilized probe on a capture support, without affecting analyte detection.

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A capture probe includes a first segment including a target-complementary region of sequence and a second segment for attaching the capture probe, or a hybridization complex that includes the capture probe, to an immobilized probe. The first segment can be configured to substantially complementary to a specific nucleic acid analyte sequence (or target sequence) so that a first segment and a target nucleic acid can hybridize to form a stable duplex (i.e., having a detectable melting point) under hybridizing conditions, such as described in the Examples. Alternatively, the first segment can be configured to nonspecifically bind to nucleic acid sequences in a sample under hybridizing conditions (see WO 2008/016988). The second segment includes a region of sequence that is complementary to a sequence of an immobilized probe. Preferably, a chimeric capture probe includes a nucleic acid homopolymer (e.g., poly-A or poly-T) that is covalently attached to the target-complementary region of the capture probe and that hybridizes under appropriate conditions to a complementary homopolymer of the immobilized probe (e.g., poly-T or poly-A, respectively) as previously described (U.S. Pat. No. 6,110,678 to Weisburg et al.). Capture probes may further comprise a third segment that acts as a closing sequence to inactivate unbound target capture probes in a capture reaction. This third segment can flank the first segment opposite the second segment (e.g., capture sequence:target hybridizing sequence:closing sequence) or it can flank the second segment opposite the first segment (e.g., closing sequence: capture sequence:target hybridizing sequence). See WO 2006/007567 and US 2009-0286249.

An immobilized probe includes a nucleic acid joined directly or indirectly to a support. The nucleic acid is complementary to a nucleic acid in the capture probe, although may or may not be the same length (number of nucleobase units) as the in the capture probe. The nucleic acid in the immobilized probe preferably contains at least six contiguous nucleobase units and can contain for example 10-45 or 10-40 or 10-30 or 10-25 or 15-25, inclusively, L-nucleobase units. The nucleic acid is preferably a homopolymer, and more preferably a homopolymer of adenine or thymine. A preferred form of immobilized probe is or includes a homopolymer of 14 thymine residues for use in combination with a capture probe including a second segment with a homopolymer of adenine residues. The nucleic acid moiety of an immobilized probe is typically provided in single-stranded form, or if not, is denatured to single-stranded form before or during use.

Any of a variety of materials may be used as a support for the immobilized probes, e.g., matrices or particles made of nitrocellulose, nylon, glass, polyacrylate, mixed polymers, polystyrene, silane polypropylene, and magnetically attractable materials. Monodisperse magnetic spheres are a preferred support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support. The linker can include one or more nucleotides not intended to hybridize to the capture probe but to act as a spacer between the nucleic acid of the immobilized probe and its support.

A "detection probe" is a nucleic acid or other molecule that binds specifically to a target sequence and which binding results, directly or indirectly, in a detectable signal to indicate the presence of the target sequence. A detection probe need not be labeled to produce a detectable signal, e.g., an electrical impulse resulting from binding the probe to its target sequence may be the detectable signal. A "labeled probe" is a probe that contains or is linked, directly or indirectly, to a label (e.g., Sambrook et al., Molecular Cloning, A Laboratory Manual, 2nd ed., Chapt. 10; U.S. Pat. No. 6,361,945, Becker et al.; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; U.S. Pat. No. 5,731,148, Becker et al.). For example, detection probes may include a non-nucleotide linker and a chemiluminescent label attached to the linker (U.S. Pat. Nos. 5,185, 439, 5,585,481 and 5,639,604, Arnold et al.). Examples of detection probes include oligonucleotides of about 5 to 50 nucleotides in length having an attached label that is detected in a homogeneous reaction, e.g., one that uses differential hydrolysis of a label on a bound or unbound probe.

Detection probes can have a nucleotide sequence that is of the same or opposite sense as a target sequence depending on the format of the assay. Detection probes can hybridize to the same or different segment of a target sequence as a capture probe. Some detection probes have an attached chemiluminescent marker, e.g., an acridinium ester (AE) compound (U.S. Pat. Nos. 5,185,439, 5,639,604, 5,585,481, and 5,656,744). In some detection probes, an acridinium ester label is attached to a central region of the probe near a region of A and T base pairs by using a non-nucleotide linker (U.S. Pat. Nos. 5,585,481 and 5,656,744, Arnold, et al.) which restricts the amines of the nucleotide bases on both sides of the AE and provides a site for intercalation. Alternatively, an AE label may be attached to the 3' or 5' terminus of the detection probe which is used in conjunction with a second oligomer that hybridizes adjacent to the detection probe on the target nucleic acid to restrict the effects of nearby amine contributed by the target nucleic acid. In some detection probes, an AE label at or near the site of a mismatch with a related non-target polynucleotide sequence, to permit discrimination between the related sequence and the target sequence that may differ by only one nucleotide because the area of the duplex around the mismatch site is sufficiently destabilized to render the AE on the probe hybridized to the related non-target sequence susceptible to hydrolysis degradation. HIV-1 and HCV may be detected using a modified form of the commercial PRO-CLEIX® ULTRIO HIV-1/HCV/HBV Assay from Gen-Probe. The modification involves replacing the D-polyA and D-polyT sequences in capture and immobilized probes with L-poly A and L-poly-T, respectively.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

Specific binding of a target capture oligomer to a target nucleic acid or target nucleic acids means binding between a single defined sequence in the first segment of a target capture oligomer and an exactly or substantially complementary segment on target nucleic acid(s) to form a stable duplex. Such binding is detectably stronger (higher signal or melting temperature) than binding to other nucleic acids in the sample lacking a segment exactly or substantially complementary to the single defined target capture oligomer sequence. Non-specific binding of a target capture oligomer to target nucleic acids means that the target capture oligomer can bind to a population of target sequences that do not share a segment having exact or substantial complementarity to a single defined target capture oligomer sequence. Such can be achieved by for example using a randomized sequence in the first segment of the capture probe.

Lack of binding between nucleic acids can be manifested by binding indistinguishable from nonspecific binding occurring between a randomly selected pair of nucleic acids lacking substantial complementarity but of the same lengths as the nucleic acids in question.

"Release" of a capture hybrid refers to separating one or more components of a capture hybrid from each other, such as separating a target nucleic acid from a capture probe, and/or a target capture oligomer from an immobilized probe. Release of the target nucleic acid strand separates the analyte from other components of a capture hybrid and makes the analyte available for binding to a detection probe. Other components of the capture hybrid may remain bound, e.g., the target capture oligomer strand to the immobilized probe on a capture support, without affecting analyte detection.

"Sensitivity" is the proportion of true positives correctly identified as such (e.g. the percentage of infected patients correctly identified as having the infection). Specificity measures the proportion of true negatives which are correctly identified (e.g. the percentage of uninfected patients who are correctly identified as not having the infection.)

Reference to a range of values also includes integers within the range and sub-ranges defined by integers in the range. Reference to any numerical value or range of numerical values should be understand as encompassing any such variation as is inherent in measuring that value other typical conditions of use.

DETAILED DESCRIPTION

I. General

Provided herein is a lysis reagent for lysing blood cells, thereby releasing RNA or other analyte in a form suitable for analysis. Preferably, the lysis reagent lysis blood cells, including red blood cells, thereby releasing RNA or other analyte in a form suitable for analysis. In one aspect, the lysis reagent lysis a sample comprising, consisting of, or consisting essentially of blood cells, thereby releasing RNA or other analyte in a form suitable for analysis. The lysis reagent comprises at least a buffer, a salt and a detergent. The reagent serves to lyse blood cells, protect a released analyte from degradation in the lysate, and is compatible with subsequent steps for analysis of the analyte, such as target capture, amplification, detection, and/or sequencing. The lysis reagent is amenable for analysis of an analyte from a pathogen or a host. Analytes are preferably nucleic acid analytes from a pathogen or from a host. More preferably, analytes are RNA analytes from a pathogen or from a host. The lysis reagent is particularly amenable for analysis of nucleic acids from pathogens infecting blood cells, including, but not limited to: hepatitis viruses, human immunodeficiency viruses, dengue viruses, west nile viruses, flaviviruses, such as zika virus, and parasitic organisms such as *Babesia* and *Plasmodium* species.

The disclosed lysis reagent results in part from identifying deficiencies with various known lysis agents for preparing and analyzing pathogen-derived RNA from red blood cells; though the lysis reagent can be used for preparing a number of components from blood cells. Known lysis agents were found to be incompatible with reagents and methods for analyzing pathogen-derived RNA, causing cell clumping, the appearance of precipitate, and the loss of magnetic beads when lysed samples were added to capture reagents. By contrast, the present lysis reagent was compatible with these methods, allowing for the lysis of blood cells in whole blood samples and the sensitive detection of the released pathogen-derived RNA following target capture and transcription mediated amplification. The present lysis reagent also inhibited degradation of the pathogen-derived RNA by nucleases and proteases following lysis and demonstrated reproducibility between samples.

II. Lysis Reagents

The present lysis reagent comprises at least a buffer, a detergent and one or both of a salt and an anti-coagulant. Buffers are present in the lysis reagent at a concentration from about 5 mM to about 150 mM. Sodium bicarbonate is one example of a suitable buffer ($NaHCO_3$). Sodium bicarbonate buffer can be present in the reagent at a concentration of, for example, from about 5 mM to about 30 mM, from about 10 mM to about 20 mM, from about 10 mM to about 15 mM, from about 15 mM to about 20 mM, from about 12 mM to about 16 mM or at about 14 mM. TRIS buffer can be present in the reagent at a concentration of, for example from about 75 mM to about 150 mM, from about 75 mM to about 125 mM, from about 100 mM to about 125 mM, from about 90 mM to about 110 mM, or at about 100 mM. Sodium phosphate buffer can be present in the reagent at a concentration of, for example, from about 5 mM to about 40 mM, from about 10 mM to about 33 mM, from about 15 mM to about 30 mM, about 30 mM, or about 15 mM. Sodium phosphate monobasic buffer can be present in the reagent at a concentration of, for example, from about 8 mM to about 40 mM, from about 10 mM to about 33 mM, from about 15 mM to about 30 mM, about 30 mM, or about 15 mM. Sodium phosphate dibasic buffer can be present in the reagent at a concentration of, for example, from about 8 mM to about 40 mM, from about 10 mM to about 33 mM, from about 15 mM to about 30 mM, about 30 mM, or about 15 mM.

The pH of the reagent can be, for example, from about 6.0 to about 10.0, from about 6.5 to about 9.0, from about 7.0 to about 8.0, from about 7.2 to about 7.6, about 7.5, about 7.3, or about 6.7. Ranges include all whole and partial numbers therein.

Detergents can act as both a lysing agent and as an inhibitor of analyte degradation following the lysis of blood cells. Detergents are particularly useful for inhibiting the degradation of nucleic acids. Exemplary detergents include Triton X-100, nonyl phenoxypolyethoxylethanol (NP-40), lithium lauryl sulfate (LLS) or sodium dodecyl sulfate (SDS). LLS is preferred. By way of example, a concentration range of detergent in the lysis reagent includes from about 2% to about 15% (v/v or w/v), from about 4% to about 10% (v/v or w/v), from about 5% to about 8% (v/v or w/v), about 6% (v/v or w/v), about 8% (v/v or w/v), or about 10% (v/v or w/v).

Salts, if present in the lysis reagent, are at a concentration from about 10 mM to about 1,000 mM. Exemplary concentration ranges for ammonium chloride in the reagent include from about 100 mM to about 1000 mM, from about 100 mM to about 800 mM, from about 100 mM to about 500 mM, from about 150 mM to about 300 mM, from about 200 mM to about 300 mM, from about 240 to about 260 mM, or about 250 mM. Exemplary concentration ranges for magnesium chloride in the reagent include from about 10 mM to about 300 mM, from about 15 mM to about 200 mM, from about 20 mM to about 100 mM, from about 25 mM to about 50 mM, from about 28 mM to about 40 mM, from about 30 mM to about 35 mM, about 33 mM, or about 30 mM. Exemplary concentration ranges for potassium chloride in the reagent include from about 10 mM to about 300 mM, from about 15 mM to about 200 mM, from about 20 mM to about 100 mM, from about 25 mM to about 50 mM, from about 28 mM to about 40 mM, from about 30 mM to about 35 mM, about 33 mM, or about 30 mM.

The anti-coagulant, if present in the lysis reagent, is at a concentration sufficient to inhibit clotting of the sample (e.g., whole blood or red blood cells). By inhibiting clotting, the anti-coagulant eliminates the need to centrifuge samples during the method to isolate red blood cells. Exemplary anti-coagulants include EDTA EDTA-Na$_2$, EGTA, heparin, or citrate. Exemplary concentrations of EDTA in the lysis reagent include from about 0.05 mM to about 15 mM, from about 0.1 mM to about 10 mM, from about 0.5 mM to about 5 mM, about 10 mM, about 2.5 mM or about 0.1 mM. Exemplary concentrations of EDTA-Naz in the lysis reagent include from about 0.05 mM to about 15 mM, from about 0.1 mM to about 10 mM, from about 0.5 mM to about 5 mM, about 10 mM, about 2.5 mM, or about 0.1 mM. Exemplary concentrations of EGTA in the lysis reagent include from about 0.05 mM to about 15 mM, from about 0.1 mM to about 10 mM, from about 0.5 mM to about 5 mM, about 7.5 mM, about 3 mM or about 1 mM.

A preferred lysis reagent includes sodium bicarbonate, ammonium chloride, LLS, and EDTA in a powder form or in a solvent, such as water, at any of the concentrations indicated above. Preferably sodium bicarbonate is at a concentration of 12 mM to 16 mM or, more preferably at 14 mM; ammonium chloride is at a concentration of 100 mM to 500 mM or, more preferably 250 mM, LLS is at a concentration of 4% to 15% or, more preferably 8% (w/v), EDTA is at a concentration of 0.01 mM to 10 mM or, more preferably, 0.1 mM or 10 mM; and the pH of the reagent is 7.2 to 7.6 or, more preferably, 7.3. Optionally, the lysis reagent consists essentially of sodium bicarbonate, ammonium chloride, LLS, EDTA, and water.

A preferred lysis reagent includes sodium phosphate, LLS, EDTA-Na$_2$, and EGTA in a powdered form or in a solvent, such as water, at any of the concentrations indicated above. Preferably, the sodium phosphate buffer is at a concentration of from about 5 mM to about 30 mM or, more preferably, 30 mM or 15 mM; the LLS is at a concentration of 4% to 15% or, more preferably 10% (w/v); the EDTA-Na$_2$ is at a concentration of 0.5 mM to 5 mM or, more preferably, 1 mM; and the EGTA is at a concentration of 0.5 mM to 5 mM or, more preferably, 1 mM; and the pH of the reagent is 6.0 to 8.0 or, more preferably, 6.7. Preferably, the sodium phosphate buffer comprises one or both of sodium phosphate monobasic and sodium phosphate dibasic. Preferably, sodium phosphate buffer comprises sodium phosphate monobasic at a concentration of from about 5 mM to about 30 mM or, more preferably, 30 mM or 15 mM. Preferably, sodium phosphate buffer comprises sodium phosphate dibasic at a concentration of from about 5 mM to about 30 mM or, more preferably, 30 mM or 15 mM. Preferably, sodium phosphate buffer comprises sodium phosphate monobasic at a concentration of from about 5 mM to about 30 mM or, more preferably, 30 mM or 15 mM and comprises sodium phosphate dibasic at a concentration of from about 5 mM to about 30 mM or, more preferably, 30 mM or 15 mM. Optionally, the lysis reagent consists essentially of sodium phosphate, detergent, EDTA-Na$_2$, EGTA, and water.

A preferred lysis reagent includes TRIS, magnesium chloride, and LLS in a powdered form or in a solvent, such as water, at any of the concentrations indicated above. Preferably TRIS is at a concentration of 75 mM to 150 mM or, more preferably 100 mM; magnesium chloride is at a concentration of 10 mM to 50 mM or, more preferably, 30 mM; the LLS is at a concentration of 4% to 15% or, more preferably 6% (w/v); and the pH of the reagent is 7.0 to 8.0 or, more preferably, 7.5. Optionally, the lysis reagent consists essentially of TRIS, magnesium chloride, and LLS, and water. Optionally, the lysis reagent contains an anti-foaming agent.

The lysis reagent can be provided as a kit also including capture probe, immobilized probe, solid support, detection probe and or primers for performing an assay on an analyte to be isolated from blood cells, including any of the analytes described below. Such a kit can include instructions for using the lysis reagent and/or performing an assay on an analyte isolated from blood cells. Reaction mixtures can be prepared from the kits, including blood cell lysis reaction mixtures, target capture reaction mixtures, nucleic acid amplification reaction mixtures, nucleic acid detection reaction mixtures, and combinations thereof. Some reaction mixtures contain the lysis reagent disclosed herein.

III. Use of Lysis Reagents

Whole blood can be obtained from a number of sources, including directly from whole blood donors or from blood banking facilities. Red blood cells can be obtained from any available source, such as whole blood or any fraction thereof that includes red blood cells, such as pelleted red blood cells. Whole blood can be human whole blood, non-human whole blood, or a combination thereof.

The lysis reagent can be admixed with blood cells for a time sufficient to induce cell lysis and cause release of molecules of desired analyte(s) from cells. Exemplary times for maintaining blood cells admixed with lysis reagent include 1-30 minutes, 2-15 minutes, 3-10 minutes, 4-6 minutes, or 5 minutes. Preferably, the time is no more than 30, 15, 10 or 5 minutes. Preferably the mixture lacks visible particles after lysis. Ranges include all whole and partial numbers therein.

The temperature of incubation of the lysis reagent with blood cells can vary. The temperature is preferably chosen to maximize extent and rate of lysis and to minimize degradation of analyte(s) or prevent inhibition of subsequent processing. Exemplary temperature ranges include 0-50° C., 5-45° C., 10-40° C., 15-37° C., 20-30° C., 22-27° C., or 25° C. Ambient temperature is suitable. Lysis of blood cells should release a sufficient amount of analyte molecules to be detectable by the methods described herein. Preferably lysis results in at least 50%, 60%, 70%, 80%, 90%, or 100% lysis of blood cells in a sample being lysed. Ranges include all whole and partial numbers therein.

The ratio at which whole blood is combined with lysis reagent can affect the extent and rate of cell lysis and protection of analyte molecules from degradation after release from lysed cells. Exemplary ratios in which whole blood is admixed with the lysis reagent include ratios of 1:1, 1:2, 1:3, 1:4, 1:5, 1:10, or in a range of ratios between 1:1 and 1:10 (v/v; whole blood:reagent). A preferred ratio is whole blood admixed with the lysis reagent at a ratio of about 1:2 to about 1:4, or 1:2, or 1:3, or 1:4 (v/v). When the sample comprises red blood cells isolated from whole blood, such as pelleted red blood cells, the red blood cells can be admixed with the lysis reagent at exemplary ratios of 1:1, 1:2, 1:3, 1:4, 1:5, 1:10, or in a range of ratios between 1:1 and 1:10 (v/v; red blood cells:reagent). Ranges include all whole and partial numbers therein.

IV. Analytes

Analytes released from blood cells, including from red blood cells, by the present reagent can be analytes from a pathogen or analytes from a host. Analytes released from blood cells, including from red blood cells, by the present lysis reagent can include nucleic acids (e.g., DNA or RNA), whole particles, proteins, and antibodies. Analytes are preferably nucleic acid analytes from a pathogen or from a host. More preferably, analytes are RNA analytes from a pathogen or from a host. Various types of RNA analytes can be detected. The RNA analytes can be ribosomal RNA (rRNA), messenger RNA (mRNA), or heterogeneous nuclear RNA (hnRNA). A preferred analyte for pathogen-derived analytes is ribosomal RNA, particularly 18S rRNA, 5S rRNA, 5.8S rRNA, or 28S rRNA.

Exemplary pathogens include those that can be detected from blood cells, including, but not limited to, hepatitis viruses, human immunodeficiency viruses, dengue viruses, west nile viruses, flaviviruses, such as zika virus, and parasitic organisms. Exemplary parasitic organisms include parasites from the genus *Babesia, Plasmodium, Trypanosoma, Leishmania, Anaplasma,* or *Toxoplasma*. Organisms of the genus *Babesia* that cause disease in humans can be *Babesia microti, Babesia divergens,* or *Babesia duncani*. Organisms of the genus *Plasmodium* can be *Plasmodium falciparum, Plasmodium malariae, Plasmodium ovale, Plasmodium vivax,* or *Plasmodium knowlesi*.

V. Assays

Analyte molecules released from lysis of blood cells are subject to analysis. Analyte molecules may or may not be separated from the lysis reagent (by centrifugation or otherwise) before analysis. Omission of a separation step can facilitate efficient work flow in performing the assay. The type of assay depends on the analyte.

A. Nucleic Acids

Analysis of nucleic acid analytes often involves steps of capture, amplification and detection. Alternatively, amplification and detection methods can be performed without prior target capture. Preferably amplification, and detection and target capture (if performed) occur without separation of analyte molecules from the lysis reagent. Thus, the entire process can be performed in a single vessel.

1. Target Capture Assay

An exemplary target capture assay can be performed as follows using one or more capture probes, an immobilized probe, a sample, and a suitable medium to permit hybridization of the target capture oligomer to the target nucleic acid and of target capture oligomer to the immobilized probe. The sample can be heated (e.g., from 65° C. to 95° C.) before performing the assay to denature any nucleic acids in double-stranded form. The components can be mixed in any order. For example the target capture oligomer can be added to the sample and hybridized with the target nucleic acid in the sample before adding the immobilized probe. However, for an automated assay, it is preferable to minimize the number of adding steps by supplying the target capture oligomer and immobilized probe at the same or substantially the same time. In this case, the order of hybridization can be controlled by performing a first hybridization under conditions in which a duplex can form between the target capture oligomer and the target nucleic acid but which exceeds the melting temperature of the duplex that would form between first and second stem segments of the capture probe and between the target capture oligomer and immobilized probe, and then performing a second hybridization under conditions of reduced stringency, preferably below the melting temperature of the duplexes formed between the first and second stem segments and between the target capture oligomer and the immobilized probe. Stringency can be reduced by lowering the temperature of the assay mix. At the higher temperature, the target binding site duplexes with the target nucleic acid. At the lower temperature, the first and second stem segments of capture probes not bound to the target nucleic acid duplex with one another and the first stem segment of capture probes bound to the target nucleic acid duplexes with the immobilized probe. For example, the higher stringency hybridization can be performed at or around 60° C. and the lower stringency hybridization by allowing cooling to room temperature or 25° C. Stringency can also be reduced by reducing salt concentration or adding or increasing concentration of a chaotropic solvent. In some methods, all steps (with the possible exception of an initial denaturation step at higher temperature to denature double stranded target) can be performed isothermally.

Following formation of the target nucleic acid:capture probe, immobilized probe hybrid (the capture hybrid complex) is separated away from other sample components by physically separating the capture support using any of a variety of known methods, e.g., centrifugation, filtration, or magnetic attraction of a magnetic capture support. The separation is preferably performed at a temperature below the melting temperature of stem-loop structures formed by target capture oligomers so that empty target capture oligomers have no opportunity to denature and thus bind to the capture probe. In some methods, the separation is performed at a temperature less than but within 10° C. of the melting temperature of the stem-loop structure (e.g., at 60° C.) to maintain stringency of hybridization conditions and consequent ability to distinguished matched and unmatched target nucleic acids.

To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., a solution containing Tris and EDTA. See e.g., U.S. Pat. No. 6,110,678) and appropriate conditions (e.g., temperature above the $T_m$ of the components) and then readjusting the conditions to permit reformation of the capture hybrid. However, for ease of handling and minimization of steps, washing preferably rinses the intact capture hybrid attached to the capture support in a solution by using conditions that maintain the capture hybrid. Preferably, capture of the target nucleic acid with washing if performed, isolates at least 70%, preferably at least 90%, and more preferably about 95% of the target nucleic acids away from other sample components. Isolated nucleic acids can be used for a number of downstream processes, such as nucleic acid amplification.

A target capture assay may also be performed as part of a real-time, biphasic, target capture and amplification method. In such a method, 500 μL of sample and 400 μL of target capture reagent (TCR) are added to reaction tubes. The TCR contains magnetic particles, components to lyse organisms present in the sample, capture oligos, a T7 initiation promoter, and an internal calibrator. Fluid in the reaction tubes is mixed for a specific time and speed to ensure the mixture is homogeneous. Reaction tubes are then transferred to a transition incubator at 43.7° C. to preheat the fluid in the reaction tubes. Reaction tubes are then transferred to an anneal incubator set at 64° C. During incubation at 64° C., any organisms present in the sample that were not previously disrupted by the lysis reagent are disrupted, causing release of the analyte. Reaction tubes are then moved to a transition incubator to start a cool down process, and are further cooled in a chiller ramp (17° C. to 19° C.), leading to binding of the T7 initiation promoter and capture of both the analyte and the internal calibrator to the magnetic particles via the capture oligos. The reaction tubes are moved to a magnetic parking station where they are subjected to magnets which pull the magnetic particles to the sides of the tubes prior to entering a wash station. In the wash station, potential interfering substances are removed from the reaction by washing the magnetic particles.

2. Amplification

A nucleic acid analyte can be amplified using methods such as isothermal amplification reactions (e.g., transcription mediated amplification (TMA), nucleic acid sequence based amplification (NASBA), loop mediated isothermal amplification, polymerase spiral reaction (PSR) (Liu, W. et al. Polymerase Spiral Reaction (PSR): A novel isothermal nucleic acid amplification method. Sci. Rep. 5, 12723; (2015)), ligase chain reaction, and other isothermal amplification methods), or temperature cycling amplification reactions (e.g., polymerase chain reaction (PCR), quantitative PCR (qPCT), real time PCR (rt-PCT), or other temperature cycling amplification methods), or other amplification methods. Detection of the amplified RNA analyte products can be performed during amplification (real-time) or following amplification (end-point).

i. Transcription Mediated Amplification

TMA has been previously described (e.g., U.S. Pat. Nos. 5,399,491, 5,554,516, 5,824,518 and 7,833,716; and also e.g., F. Gonzales and S. McDonough. Applications of Transcription-Mediated Amplification to Quantification of Gene Sequences. Gene Amplification. 1998 Ed. Francois Ferre, Birkhauser, Boston. PP. 189-204). In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer binds specifically to the analyte nucleic acid at its target sequence and a reverse transcriptase (RT) extends the 3' end of the promoter primer using the target strand as a template to create a cDNA copy, resulting in a RNA:cDNA duplex. RNase activity (e.g., RNase H of RT enzyme) digests the RNA of the RNA:cDNA duplex and a second primer binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce about 100 to 1000 RNA transcripts (amplified copies or amplicons) complementary to the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer as well as the 3' end of the cDNA to create a dsDNA that contains a functional promoter to which the RNA polymerase binds and transcribes additional amplicons that are complementary to the target strand. Autocatalytic cycles that use these steps repeatedly during the reaction produce about a billion-fold amplification of the initial target sequence. Optionally, amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

TMA may also be performed as part of a real-time, biphasic, target capture and amplification method. In such a method, TMA can be performed by adding amplification reagent (50 µL/test) to reaction tubes containing captured analyte molecules and mixing in an amplification load station. The amplification reagent contains oligos and components necessary to build nucleic acids. The reaction tubes are moved to a transition incubator at 43.7° C. to increase the temperature of the liquid in the reaction tubes, which are then moved back to the amplification load station where enzyme (25 µL/test) is added. Reaction tubes are moved to the amplification incubator set at 42.7° C. and remain in the incubator for five minutes, during which the first rounds of amplification are initiated. Reaction tubes are moved back to the amplification load station where promoter reagent (25 µL/test) is added. Reaction tubes are moved back to the amplification incubator for further rounds of analyte amplification. The promoter reagent contains oligos and torches. The torches are complementary to the analyte or internal calibrator and fluoresce when bound, generating signal in real-time. The signals for the target and internal calibrator preferably have different wavelengths and can be distinguished.

ii. Polymerase Chain Reaction

Alternatively, PCR amplification (e.g., reverse transcriptase or real-time PCR) can be used for amplification. PCR can be performed with or without prior release of the target nucleic acid from the capture complex. The PCR reaction can be performed in the same vessel (e.g., a microfuge tube) as the capture step. The PCR reaction involves thermocycling between a high temperature of about 95° C. (e.g., 90-99° C.) for dissociation and a low temperature of about 60° C. e.g., 40-75, or 50-70 or 55-64° C.) for annealing. Typically, the number of complete thermocycles is at least 10, 20, 30 or 40. PCR amplification is performed using one or more primer pairs. A primer pair used for PCR amplification includes two primers complementary to opposite strands of a target nucleic acid flanking the region desired to be sequenced. For sequencing most of a viral genome (e.g., more than 50, 75 or 99%), the primers are preferably located close to the ends of the viral genome. For amplification of related molecules (e.g., mutant forms of the same virus present in a patient sample), the primers are preferably complementary to conserved regions of the target nucleic acid likely to be present in most members of the population. PCR amplification is described in PCR Technology: Principles and Applications for DNA Amplification (ed. H. A. Erlich, Freeman Press, NY, NY, 1992); PCR Protocols: A Guide to Methods and Applications (eds. Innis, et al., Academic Press, San Diego, CA, 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

3. Detection

Detection of a nucleic acid analyte can be performed following capture and either during (real-time) or following (end-point) amplification by using any known method. The amplification product of RNA is often in the form of DNA resulting from RT-PCR or RNA copies resulting from TMA. Amplified nucleic acids may be detected in solution phase or by concentrating them in or on a matrix and detecting labels associated with them (e.g., an intercalating agent such as ethidium bromide). Some detection methods use probes complementary to a sequence in the amplified product and detect the presence of the probe:product complex, or use a complex of probes to amplify the signal detected from amplified products (e.g., U.S. Pat. Nos. 5,424,413, 5,451, 503 and 5,849,481). Other detection methods use a probe in which signal production is linked to the presence of the target sequence because a change in signal results only when the labeled probe binds to amplified product, such as in a molecular beacon, molecular torch, or hybridization switch probe (e.g., U.S. Pat. Nos. 5,118,801, 5,210,015, 5,312,728, 5,538,848, 5,541,308, 5,656,207, 5,658,737, 5,925,517, 6,150,097, 6,361,945, 6,534,274, 6,835,542, and 6,849,412; and U.S. Pub. No. 2006/0194240 A1). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that was amplified.

4. Sequencing

Following amplification, a nucleic acid analyte as well as or instead of undergoing qualitative or quantitative detection can be sequenced. Purification if desired can be performed on a silica column (e g., a Qiagen gravity flow column). The target nucleic acid binds to the column, where it can be washed and then eluted. Alternatively, purification can be performed using a nucleic acid probe-based purification system (e.g., U.S. Pat. No. 6,110,678 or U.S. Pat. No. 8,034,554, US 2013/0209992 or US 2009/0286249, or. WO 2012/037531 or WO 2013/116774). The amplified analyte DNA can also be adapted for some sequencing formats by attachment of an adapter. The amplified DNA can be tailed by Klenow-mediated addition of nucleotides (usually a homopolymer) followed by annealing to an oligonucleotide complementary to the added tail, and ligation. Depending on the sequencing platform used, special adaptors are ligated to the template before sequencing. For example, a SMRT bell adapter is ligated to the sample template for sequencing with a Pacific Biosciences' PacBio RS sequencer (see, e.g., Travers et al. Nucl. Acids Res. (2010) 38 (15): e159).

The amplified target nucleic acid is suitable for sequence analysis by a variety of techniques. The capture of target nucleic acid can be coupled to several different formats of so-called next generation and third generation sequencing methods. Such methods can sequence millions of target templates in parallel. Such methods are particularly useful when the target nucleic acid is a heterogeneous mixture of variants. Among the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a target capture oligomer provides a suitable starting material for emulsion PCR. The beads are mixed with PCR reagents and emulsion oil to create individual micro reactors containing single beads (Margulies et al., Nature 437, 376-80 (2005)). The emulsion is then broken and the individual beads with amplified DNA are sequenced. The sequencing can be pyrosequencing performed for example using a Roche 454 GS FLX sequencer (454 Life Sciences, Branford, CT 06405). Alternatively, sequencing can be ligation/detection performed for example using an ABI SOLiD Sequencing System (Life Technologies, Carlsbad, CA 92008). In another variation, analyte nucleic acids are eluted from beads having target capture oligomers and are immobilized in different locations on an array (e.g., the HiScanSQ (Illumina, San Diego, CA 92121)). The target nucleic acids are amplified by bridge amplification and sequenced by template directed incorporation of labeled nucleotides, in an array format (Illumina). In another approach, analyte nucleic acids are eluted from the target capture oligomer and single molecules are analyzed by detecting in real-time the incorporation nucleotides by a polymerase (single molecule real time sequencing or SMRT sequencing). The nucleotides can be labeled nucleotides that release a signal when incorporated (e.g., Pacific Biosciences, Eid et al., Sciences 323 pp. 133-138 (2009) or unlabeled nucleotides, wherein the system measures a chemical change on incorporation (e.g., Ion Torrent Personal Genome Machine (Life Technologies)).

Although captured target nucleic acids can be sequenced by any technique, third generation, next generation or massively parallel methods offer considerable advantages over Sanger and Maxam Gilbert sequencing. Several groups have described an ultrahigh-throughput DNA sequencing procedure (see. e.g., Cheeseman, U.S. Pat. No. 5,302,509, Metzker et al., Nucleic Acids Res. 22: 4259 (1994)). The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi, Science 281, 363 (1998); Binladin et al., PLoS ONE, issue 2, e197 (February 2007); Rehman et al., American Journal of Human Genetics, 86, 378 (March 2010); Lind et al., Next Generation Sequencing: The solution for high-resolution, unambiguous human leukocyte antigen typing, Hum. Immunol. (2010), doi 10.1016/jhumimm 2010.06.016 (in press); Shafer et al., J Infect Dis. 1; 199(5):610 (2009)). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. More recent work performs DNA sequencing by a synthesis method mostly focused on a photocleavable chemical moiety that is linked to a fluorescent dye to cap the 3'—OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041, 812; Sood et al, US Pat. App. No. 2004-0152119; Eid et al., Science 323, 133 (2009)). In sequencing-by-synthesis methodology, DNA sequences are being deduced by measuring pyrophosphate release on testing DNA/polymerase complexes with each deoxyribonucleotide triphosphate (dNTP) separately and sequentially. See Ronaghi et al., Science 281: 363 365 (1998); Hyman, Anal. Biochem. 174, 423 (1988); Harris, U.S. Pat. No. 7,767,400.

B. Other Analytes

Antibodies, proteins, particles and other analytes can be detected by formats such as immunoprecipitation, Western blotting, ELISA, radioimmunoassay, competitive and immunometric assays. See Harlow & Lane, Antibodies: A Laboratory Manual (CSHP NY, 1988); U.S. Pat. Nos. 3,791, 932; 3,839,153; 3,850,752; 3,879,262; 4,034,074, 3,791, 932; 3,817,837; 3,839,153; 3,850,752; 3,850,578; 3,853, 987; 3,867,517; 3,879,262; 3,901,654; 3,935,074; 3,984, 533; 3,996,345; 4,034,074; and 4,098,876. Sandwich assays are a preferred format (see U.S. Pat. Nos. 4,376,110, 4,486,530, 5,914,241, and 5,965,375).

Competitive assays can also be used. In some methods, analyte antigen in a sample competes with exogenously supplied labeled analyte antigen for binding to an antibody detection reagent. The amount of labeled analyte antigen bound to the antibody is inversely proportional to the amount of analyte antigen in the sample. The antibody can be immobilized to facilitate separation of the bound complex from the sample prior to detection.

Lateral flow devices can also be used for detecting an analyte. Fluid is applied to a test strip that has been treated with a sample in which an analyte may be present. Labelled binding molecules pass through the strip and can be captured as they pass into a specific zone containing the sample with the analyte.

VI. Sensitivity

The present methods can provide a high sensitivity of detection of an analyte from blood cells. For pathogen-derived RNA analytes, sensitivity can be expressed as a minimum number of pathogenic RNA copies present in a volume of whole blood. The volume of whole blood can be that contacted with lysis reagent directly, or can be that used to prepare a blood fraction, such as pelleted red cells, which are in turn contacted with the lysis reagent. Preferably the methods detect the presence of pathogenic RNA in whole blood with a sensitivity of about $2\times10^3$ copies of ribosomal RNA/mL (equivalent to one parasite/1 mL) of whole blood or better, $2\times10^3$ copies/5 mL of whole blood or better, $2\times10^3$ copies/10 mL of whole blood or better, $2\times10^3$ copies/50 mL of whole blood or better, or $2\times10^3$ copies/100 mL of whole blood or better. Preferably the methods detect the presence of pathogenic RNA in whole blood with a sensitivity of about $8\times10^3$ copies of ribosomal RNA/mL (equivalent to four parasites/1 mL) of whole blood or better, $8\times10^3$ copies/5 mL of whole blood or better, $8\times10^3$ copies/10 mL of whole blood or better, $8\times10^3$ copies/50 mL of whole blood or better, or $8\times10^3$ copies/100 mL of whole blood or better. Preferably the methods detect the presence of pathogenic RNA in whole blood with a sensitivity of about $24\times10^3$ copies of ribosomal RNA/mL (equivalent to 12 parasites/1 mL) of whole blood or better, $24\times10^3$ copies/5 mL of whole blood or better, $24\times10^3$ copies/10 mL of whole blood or better, $24\times10^3$ copies/50 mL of whole blood or better, or $24\times10^3$ copies/100 mL of whole blood or better.

EXAMPLES

Example 1. Analysis of Reagents for Cell Lysis and Stabilization of *Babesia* RNA The purpose of this example was to identify a lysis reagent that would effectively and preferentially lyse red blood cells in human whole blood, stabilize analyte(s) in the lysed sample, and inhibit the activity of RNAses. Preferential lysis of red blood cells over other cellular components of blood means that the percentage of red blood cells lysed is higher than that of other cellular components present in the sample being analyzed, the other cell types being assessed in the aggregate. In this example, the analyte is a pathogen-derived RNA analyte, 18S ribosomal RNA from *Babesia* parasites. To be compatible with Gen-Probe's Target Capture Technology using magnetic beads, the lysis reagent should preferably result in a homogeneous lysate for efficient target capture.

In this first example, the PAXgene™ Blood RNA System (BD Biosciences), Lysis Reagent A and Lysis Reagent B were evaluated for *Babesia* sample preparation. The PAXgene reagent contained in each tube comprises the active compound tetradecyltrimethylammonium oxalate (TDT-MAO), a quarternary ammounium salt known to lyse cell membranes and act as a stabilizing reagent. Lysis Reagent A, was an aqueous solution of 14 mM sodium bicarbonate, 250 mM ammonium chloride, 5% (w/v) LLS, and 0.1 mM EDTA, at a pH of 7.4. Lysis Reagent B, was an aqueous solution of 14 mM sodium bicarbonate, 250 mM ammonium chloride, 8% (w/v) LLS, and 0.1 mM EDTA, at a pH of 7.3.

The sample used for preparation was human whole blood spiked with *Babesia*-infected hamster blood. Infected hamster whole blood was serially diluted by combining 10 uL of infected hamster blood with 90 uL of fresh human donor blood (uninfected). Each of these serial dilutions were then combined with 900 uL of fresh human donor blood to provide 1 mL samples. Each 1 mL sample was first combined with 3 mL of lysis reagent from a PAXgene tube at room temperature and allowed to rock for 5 minutes to induce cell lysis. 500 µL of the lysed sample was then added to 500 µL of a Target Capture Reagent (TCR). Gen-Probe, Procleix, and Aptima TCRs were evaluated. Following addition of the lysed sample to the TCR, a white precipitate formed. Therefore, the PAXgene system was unsuitable for whole blood lysis, capture, amplification and detection of *Babesia* using Gen-Probe's target capture, amplification and detection reagents.

In a next experiment, a lysis reagent of 250 mM ammonium chloride (ACL), buffered with 14 mM sodium bicarbonate and containing LLS and EDTA, was evaluated. Human whole blood was spiked with *Babesia*-infected hamster blood at a dilution ranging from $1\times10^{-5}$ to $1\times10^{-8}$, as generally described above. One mL of spiked whole blood was then admixed with 3 mL of Lysis Reagent A for 5 minutes at 25° C. to induce red blood cell lysis. Following the addition of 500 µL of the lysed sample to 500 µL TCR, no precipitate was observed. Target capture was performed as generally described in U.S. Pat. No. 6,110,678. *Babesia* 18S rRNA was detected in each sample by transcription-mediated amplification (U.S. Pat. Nos. 5,399,491, 5,554,516, 5,824,518 and 7,833,716). Six (6) replicates of each dilution condition were amplified and detected. Parasite load was determined based on statistically identifying the dilution to contain about 1 parasite per mL. In addition, a serial dilution of an IVT stock with a known concentration was amplified and detected in separate wells of the reaction in order to provide a curve for calculating parasite load in each amplified/detected dilution of the hamster blood. Target capture oligomers, primers and probes used to capture, amplify and detect *Babesia* 18S rRNA in the samples were as follows:

TABLE 1

| FUNCTION | Sequence (5'-3') |
| --- | --- |
| non T7 Primer | ACAGGGAGGTAGTGACAAG (SEQ ID NO: 1) |
| T7 Primer | AATTTAATACGACTCACTATAGGGAGACTGGAATTA CCGCGGCTGCTGG (SEQ ID NO: 2) |
| AE Probe | ACCCUUCCCAGAGUAUCAAU (SEQ ID NO: 3) |
| TCO | GGAUUGGGUAAUUUGCGCGCCUUUAAAAAAAAAAAA AAAAAAAAAAAAAAAAA (SEQ ID NO: 4) |

Amplification and detection results from each of the conditions mentioned above show that Lysis Reagent A effectively lysed red blood cells to release *Babesia* 18S rRNA for subsequent analysis. Comparison of the *Babesia* rRNA detected in each of these samples of the serial dilution to the results from the serially diluted IVT showed a limit of detection as low as 0.01 parasites per mL.

Additional lysis reagents were evaluated for their lysis of blood cells and detection of pathogen derived analytes.

Example 2. Evaluation of Additional Blood Cell Lysis Reagents

A study of lysis reagents was performed to evaluate their ability to effectively lyse blood cells and release analytes for subsequent evaluation. Nucleic acid analytes were evaluated in this example using a TMA amplification and detection reaction to identify 18S rRNA from *Babesia* parasite, as described herein.

The sample used in this example was *Babesia* infected human whole blood, determined to be positive for *Babesia* by PCR. Parasitemia was determined by serially diluting the *Babesia* infected blood into uninfected blood, then increasing the volume of each dilution to 1 mL using uninfected blood, mixing the 1 mL dilution with 3 mL of Lysis Reagent A, and then performing capture, amplification and detection reactions as described in Example 1, above. Parasite load in the stock infected human blood sample was determined based on statistically identifying the dilution to contain about 1 parasite per mL and then back calculating to the stock infected blood sample. The infected blood sample was then separately diluted to provide 12 parasite/mL (12 p/mL) and 4 parasite/mL (4 p/mL) dilutions at a total volume of 1 mL, as generally described. The 12 p/mL and the 4 p/mL were each used in the below assays.

Lysis reagent C was made similarly to Lysis Reagent B, but the concentration of EDTA was increased to 10 mM. Lysis reagent D was an aqueous solution of 15 mM sodium phosphate monobasic, 15 mM sodium phosphate dibasic, 10% (w/v) LLS, 1 mM EGTA, and 1 mM EDTA-Na$_2$ dihydride, at a pH of 6.7. Lysis reagent E was an aqueous solution of 100 mM TRIS 30 mM magnesium chloride, and 6% (w/v) LLS, at pH 7.5. Separate spiked whole blood samples (described above) were each lysed with one of lysis reagents C-E at a ratio of 1:2 or 1:4 (blood sample:lysis reagent) and tested at 36 to 72 replicates per condition, as identified in Tables 2-4. Reactive samples were determined to be those with an RLU value greater than 100,000 RLU. *Babesia* 18S rRNA was detected in each sample using Procleix TCR and amplification by TMA as described above. Conditions were evaluated for sensitivity, stability, and robustness. Results for lysis reagents C-E are shown in Table 2, Table 3, Table 4.

TABLE 2

Sensitivity

| Ratio | Concentration | Lysis Reagent | Number of Reactions | Number Reactive | Percent Reactive |
|---|---|---|---|---|---|
| 1:2 | 12 p/mL | C | 71 | 70 | 98.5% |
|  |  | D | 72 | 72 | 100.0% |
|  |  | E | 72 | 72 | 100.0% |
|  | 4 p/mL | C | 72 | 50 | 69.4% |
|  |  | D | 72 | 66 | 91.7% |
|  |  | E | 69 | 54 | 78.3% |
| 1:4 | 12 p/mL | C | 72 | 72 | 100.0% |
|  |  | D | 72 | 72 | 100.0% |
|  |  | E | 72 | 72 | 100.0% |
|  | 4 p/mL | C | 72 | 66 | 91.7% |
|  |  | D | 72 | 63 | 87.5% |
|  |  | E | 72 | 67 | 93.1% |

TABLE 3

Stability: One Day.

| Ratio | Conc. | Lysis Reagent | Day 0 Number of Reactions | Day 0 Number Reactive | Day 0 Percent Reactive | Day 1 (stored at 4° C.) Number of Reactions | Day 1 (stored at 4° C.) Number | Day 1 (stored at 4° C.) Percent |
|---|---|---|---|---|---|---|---|---|
| 1:2 | 12 p/mL | C | 35 | 35 | 100.0% | 36 | 34 | 94.4% |
|  |  | D | 36 | 36 | 100.0% | 36 | 35 | 97.2% |
|  |  | E | 36 | 36 | 100.0% | 36 | 36 | 100.0% |
|  | 4 p/mL | C | 36 | 28 | 77.8% | 36 | 20 | 55.6% |
|  |  | D | 36 | 31 | 86.1% | 36 | 30 | 83.3% |
|  |  | E | 36 | 27 | 75.0% | 36 | 33 | 91.7% |
| 1:4 | 12 p/mL | C | 36 | 36 | 100.0% | 36 | 36 | 100.0% |
|  |  | D | 36 | 36 | 100.0% | 36 | 36 | 100.0% |
|  |  | E | 36 | 36 | 100.0% | 36 | 36 | 100.0% |
|  | 4 p/mL | C | 36 | 32 | 88.9% | 36 | 35 | 97.2% |
|  |  | D | 36 | 31 | 86.1% | 36 | 36 | 100.0% |
|  |  | E | 36 | 33 | 91.7% | 36 | 35 | 97.2% |

TABLE 4

Stability: Three Day.

| Ratio | Conc. | Lysis Reagent | Day 0 Number of Reactions | Day 0 Number Reactive | Day 0 Percent Reactive | Day 3 (stored at 4° C.) Number of Reactions | Day 3 (stored at 4° C.) Number Reactive | Day 3 (stored at 4° C.) Percent Reactive |
|---|---|---|---|---|---|---|---|---|
| 1:2 | 12 p/mL | C | 36 | 35 | 97.2% | 36 | 12 | 33.3% |
|  |  | D | 36 | 36 | 100.0% | 36 | 36 | 100.0% |
|  |  | E | 36 | 36 | 100.0% | 36 | 25 | 69.4% |
|  | 4 p/mL | C | 36 | 22 | 61.1% | 36 | 9 | 25.0% |
|  |  | D | 36 | 35 | 97.2% | 36 | 27 | 75.0% |
|  |  | E | 36 | 27 | 81.8% | 36 | 24 | 66.7% |

TABLE 4-continued

Stability: Three Day.

| Ratio | Conc. | Lysis Reagent | Day 0 | | | Day 3 (stored at 4° C.) | | |
|---|---|---|---|---|---|---|---|---|
| | | | Number of Reactions | Number Reactive | Percent Reactive | Number of Reactions | Number Reactive | Percent Reactive |
| 1:4 | 12 p/mL | C | 36 | 36 | 100.0% | 18 | 18 | 100.0% |
| | | D | 36 | 36 | 100.0% | 24 | 24 | 100.0% |
| | | E | 36 | 36 | 100.0% | 24 | 24 | 100.0% |
| | 4 p/mL | C | 36 | 34 | 94.4% | 36 | 31 | 86.1% |
| | | D | 36 | 32 | 88.9% | 36 | 29 | 80.6% |
| | | E | 36 | 34 | 94.4% | 36 | 32 | 88.9% |

These data show that lysis reagents C-E performed well in lysing whole blood and releasing pathogen-derived analytes from blood cells for subsequent analysis. The analytical sensitivity of a TMA assay for amplification and detection of *Babesia* 18S rRNA obtained from blood cells using lysis reagents C-E was at least as low as 4 p/mL and at a dilution of lysis buffer to whole blood as low as 4:1. A loss of sensitivity was observed following storage at 4° C. after three days, as seen by the large variability in results. This loss in sensitivity was readily observable in samples having a 2:1 dilution and 4 p/mL.

Although the invention has been described in detail for purposes of clarity of understanding, certain modifications may be practiced within the scope of the appended claims. All publications including accession numbers, websites and the like, and patent documents cited in this application are hereby incorporated by reference in their entirety for all purposes to the same extent as if each were so individually denoted. To the extent difference version of a sequence, website or other reference may be present at different times, the version associated with the reference at the effective filing date is meant. The effective filing date means the earliest priority date at which the accession number at issue is disclosed. Unless otherwise apparent from the context any element, embodiment, step, feature or aspect of the invention can be performed in combination with any other.

What is claimed is:

1. A composition comprising a lysis reagent admixed with whole blood, wherein the reagent comprises (i) sodium phosphate, (ii) lithium lauryl sulfate (LLS) at a concentration of from about 8% (w/v) to about 10% (w/v), (iii) EDTA-Na$_2$ at a concentration of from about 0.5 mM to about 5 mM, and (iv) EGTA at a concentration of from about 0.5 mM to about 5 mM, wherein the reagent has a pH that is greater than 5.5, and wherein the reagent does not include a chloride containing salt; and wherein the ratio of the reagent to the whole blood is about 4:1.

2. The composition of claim 1, wherein the sodium phosphate is present in the reagent at a concentration of from about 10 mM to about 33 mM.

3. The composition of claim 2, wherein the sodium phosphate comprises about 15 mM sodium phosphate monobasic and about 15 mM sodium phosphate dibasic.

4. The composition of claim 1, wherein the EDTA-Na$_2$ is present in the reagent at a concentration of about 1 mM.

5. The composition of claim 4, wherein the EGTA is present in the reagent at a concentration of about 1 mM.

6. The composition of claim 1, wherein the LLS is present in the reagent at a concentration of about 10% (w/v).

7. A target capture reaction mixture comprising:
(a) a lysis reagent admixed with whole blood,
wherein the reagent comprises (i) sodium phosphate, (ii) lithium lauryl sulfate (LLS) at a concentration of from about 8% (w/v) to about 10% (w/v), (iii) EDTA-$Na_2$ at a concentration of from about 0.5 mM to about 5 mM, and (iv) EGTA at a concentration of from about 0.5 mM to about 5 mM, wherein the reagent has a pH that is greater than 5.5, and wherein the reagent does not include a chloride containing salt; and
wherein the ratio of the reagent to the whole blood is about 4:1; and
(b) an immobilized probe for immobilizing a nucleic acid analyte released from blood cells in the whole blood, wherein the immobilized probe is attached to a solid support.

8. The reaction mixture of claim 7, wherein the sodium phosphate is present in the reagent at a concentration of from about 10 mM to about 33 mM.

9. The reaction mixture of claim 8, wherein the sodium phosphate comprises about 15 mM sodium phosphate monobasic and about 15 mM sodium phosphate dibasic.

10. The reaction mixture of claim 7, wherein the EDTA-$Na_2$ is present in the reagent at a concentration of about 1 mM.

11. The reaction mixture of claim 10, wherein the EGTA is present in the reagent at a concentration of about 1 mM.

12. The reaction mixture of claim 7, wherein the LLS is present in the reagent at a concentration of about 10% (w/v).

13. The reaction mixture of claim 7, further comprising a capture probe comprising a first segment complementary to the nucleic acid analyte and a second segment complementary to the immobilized probe.

14. The reaction mixture of claim 7, wherein the solid support is a magnetic bead solid support.

15. The reaction mixture of claim 7, wherein the nucleic acid analyte is an RNA.

16. The reaction mixture of claim 15, wherein the RNA is a pathogen-derived RNA.

17. The reaction mixture of claim 7, wherein the pathogen is selected from the group consisting of hepatitis viruses, human immunodeficiency viruses, dengue viruses, west nile viruses, flaviviruses, and parasitic organisms.

18. The reaction mixture of claim 17, wherein the pathogen is a parasitic organism selected from the group consisting of: parasites from the genus *Babesia*, parasites from the genus *Plasmodium*, parasites from the genus *Trypanosoma*, parasites from the genus *Leishmania*, parasites from the genus *Anaplasma*, and parasites from the genus *Toxoplasma*.

19. The reaction mixture of claim 18, wherein the parasitic organism is selected from the group consisting of *Babesia microti*, *Babesia divergens*, and *Babesia duncani*.

20. The reaction mixture of claim 18, wherein the parasitic organism is selected from the group consisting of *Plasmodium falciparum*, *Plasmodium malariae*, *Plasmodium ovale*, *Plasmodium vivax*, and *Plasmodium knowlesi*.

* * * * *

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
acagggaggt agtgacaag                                                   19

<210> SEQ ID NO 2
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 2
aatttaatac gactcactat agggagactg gaattaccgc ggctgctgg                  49

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
acccuuccca gaguaucaau                                                  20

<210> SEQ ID NO 4
<211> LENGTH: 54
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: dT3dA30_tail_(2nd-segment)
<222> LOCATION: (22)..(54)

<400> SEQUENCE: 4
ggauugggua auuugcgcgc ctttaaaaaa aaaaaaaaaa aaaaaaaaaa aaaa          54

<210> SEQ ID NO 5
<211> LENGTH: 1205
<212> TYPE: RNA
<213> ORGANISM: Artificial Sequence
<220> FEATURE:
<223> OTHER INFORMATION: Synthetic Oligonucleotide

<400> SEQUENCE: 5
gggcgaauug gguaccgggc cccccucga ggucgacgcu aguauaagc uuuuauacag       60 cgaaacugcg aauggcucau uaaaacaguu auaguuuauu ugauguucgu uuuacaugga    120
uaaccguggu aauucuaggg cuaauacaug cucgaggcgc guuuucgcgu ggcguuuauu    180
agacuuuaac caacccuucg gguaaucggu gauucauaaa aaauuagcga aucgcauggc    240
uuugccggcg auguaucauu caaguuucug accuaucagc uuuggacggu aggguauugg    300
ccaccggggc gacgacgggu gacggggaau uggggucga uuccggagag ggagccugag    360
aaacggcuac cacaucuaag gaaggcagca ggcgcgcaaa uuacccaauc cugacacagg    420
gagguaguga caagaaauaa caauacaggg cuuaaagucu uguaauugga augaugggaa    480
ucuaaacccu ucccagagua ucaauuggag ggcaagucug gugccagcag ccgcgguaau    540
uccagcucca auagcguaua uuaaaguugu ugcaguuaaa aagcucguag uugaauuucu    600
gccuugucau uaaucucgcu uccgagcguu uuuuauuga cuuggcaucu ucuggauuug    660
gugccuucgg guacuauuuu ccaggauuua cuuugagaaa acuagagugu uucaaacagg    720
cauucgccuu gaauacuaca gcauggaaua augaaguagg acuuugguuc uauuuuguug    780
guuauugagc cagaguaaug guuaauagga gcaguugggg gcauucguau uuaacuguca    840
gaggugaaau ucuuagauuu guuaaagacg aacuacugcg aaagcauuug ccaaggaugu    900
uuucauuaau caagaacgaa aguuaggggga ucgaagacga ucagauaccg ucguaguccu    960
aaccauaaac uaugccgacu agagauugga ggucgucagu uuaaacgacu ccuucagcac   1020
cuugagagaa aucaaagucu uuggguucug ggggaguau ggucgcaagu cugaaacuua   1080
aaggaauuga cggaagggca ccaccaggcg uggagccugc ggcuuaauuu gacucaacac   1140
gggaaaccuc accaggucca gacauagaga ggauugacag auugauagcu cuucuugau   1200 gaauu                                                               1205
```